US011337706B2

(12) United States Patent
Soto Del Valle et al.

(10) Patent No.: US 11,337,706 B2
(45) Date of Patent: May 24, 2022

(54) ANEURYSM TREATMENT DEVICE

(71) Applicant: DePuy Synthes Products, Inc., Raynham, MA (US)

(72) Inventors: Ariel Soto Del Valle, Raynham, MA (US); Lacey Gorochow, Raynham, MA (US); Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 208 days.

(21) Appl. No.: 16/366,235

(22) Filed: Mar. 27, 2019

(65) Prior Publication Data
US 2020/0305886 A1 Oct. 1, 2020

(51) Int. Cl.
*A61B 17/12* (2006.01)
*A61M 25/00* (2006.01)

(52) U.S. Cl.
CPC .... *A61B 17/12118* (2013.01); *A61B 17/1214* (2013.01); *A61B 2017/12054* (2013.01); *A61M 2025/0042* (2013.01)

(58) Field of Classification Search
CPC .......... A61B 17/12118; A61B 17/1214; A61B 2017/12054; A61B 17/12031; A61B 2017/00867; A61B 17/12145; A61B 17/12172; A61B 17/12113; A61B 17/12154; A61B 2017/1205; A61M 2025/0042

See application file for complete search history.

(56) References Cited

U.S. PATENT DOCUMENTS

| 2,849,002 | A | 8/1958 | Oddo |
| 3,480,017 | A | 11/1969 | Shute |
| 4,085,757 | A | 4/1978 | Pevsner |
| 4,282,875 | A | 4/1981 | Serbinenko et al. |
| 4,364,392 | A | 12/1982 | Strother et al. |
| 4,395,806 | A | 8/1983 | Wonder et al. |
| 4,517,979 | A | 5/1985 | Pecenka |
| 4,545,367 | A | 10/1985 | Tucci |
| 4,836,204 | A | 6/1989 | Landymore et al. |
| 4,991,602 | A | 2/1991 | Amplatz et al. |

(Continued)

FOREIGN PATENT DOCUMENTS

| CA | 2395796 A1 | 7/2001 |
| CA | 2 431 594 A1 | 9/2002 |

(Continued)

OTHER PUBLICATIONS

Altes et al., Creation of Saccular Aneurysms in the Rabbit: A Model Suitable for Testing Endovascular Devices. AJR 2000; 174: 349-354.

(Continued)

*Primary Examiner* — Kelly J Bekker
*Assistant Examiner* — Andrew P. Restaino
(74) *Attorney, Agent, or Firm* — Troutman Pepper Hamilton Sanders LLP

(57) ABSTRACT

An implant having an elongated portion and an expandable braided sack portion can be delivered through a catheter and implanted in an aneurysm such that elongated portion loops within the braided sack, the braided sack contacts a majority or all of the aneurysm wall, and the braided sack at least partially occludes the aneurysm neck.

6 Claims, 12 Drawing Sheets

(56) References Cited

U.S. PATENT DOCUMENTS

| | | |
|---|---|---|
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Gia et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 * | 2/2002 | Greenhalgh ..... A61B 17/12022 606/200 |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lilip Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |

(56) References Cited

U.S. PATENT DOCUMENTS

| | | |
|---|---|---|
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1* | 10/2015 | Lorenzo ........... A61B 17/12145 606/200 |
| 2015/0313605 A1 | 11/2015 | Griffin |
| 2015/0342613 A1 | 12/2015 | Aboytes et al. |
| 2015/0374483 A1 | 12/2015 | Janardhan et al. |

(56) References Cited

U.S. PATENT DOCUMENTS

| | | |
|---|---|---|
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero |
| 2017/0079680 A1 | 3/2017 | Bowman |
| 2017/0079717 A1 | 3/2017 | Walsh et al. |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0114350 A1 | 8/2017 | Shimizu et al. |
| 2017/0215902 A1 | 8/2017 | Leynov et al. |
| 2017/0216484 A1 | 8/2017 | Cruise et al. |
| 2017/0224350 A1* | 8/2017 | Shimizu ............ A61B 17/1214 |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340333 A1 | 11/2017 | Badruddin et al. |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0000477 A1 | 1/2020 | Nita et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 10/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |

(56) References Cited

FOREIGN PATENT DOCUMENTS

| | | |
|---|---|---|
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015160721 A1 | 10/2015 |
| WO | 2015171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2012/034135 A1 | 3/2021 |

OTHER PUBLICATIONS

Schaffer, Advanced Materials & Processes, Oct. 2002, pp. 51-54.
Extended European Search Report dated May 2, 2019 in corresponding European Application No. 18214052.5, 11 pages.
Extended European Search Report issued in corresponding European Patent Application No. 19 21 5277 dated May 12, 2020, 11 pages.

* cited by examiner

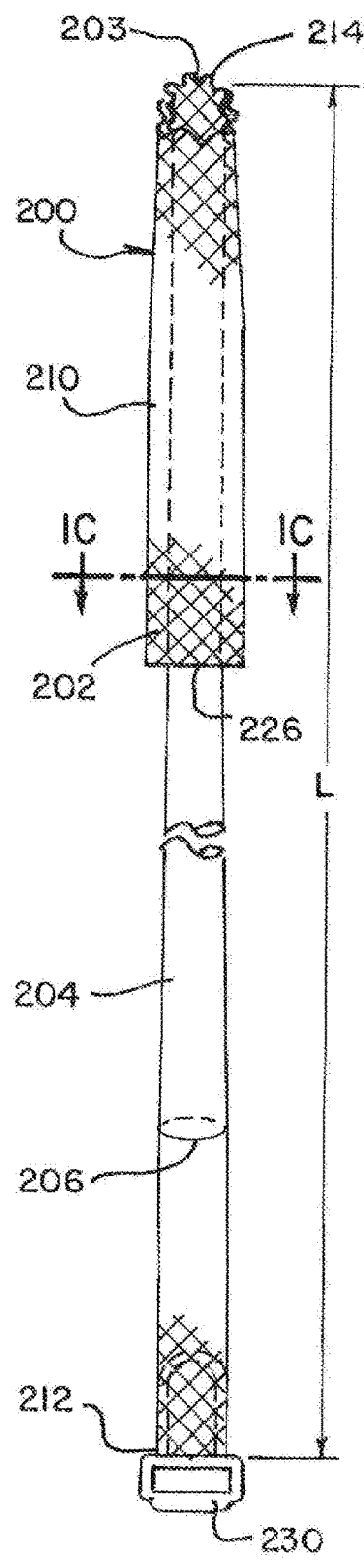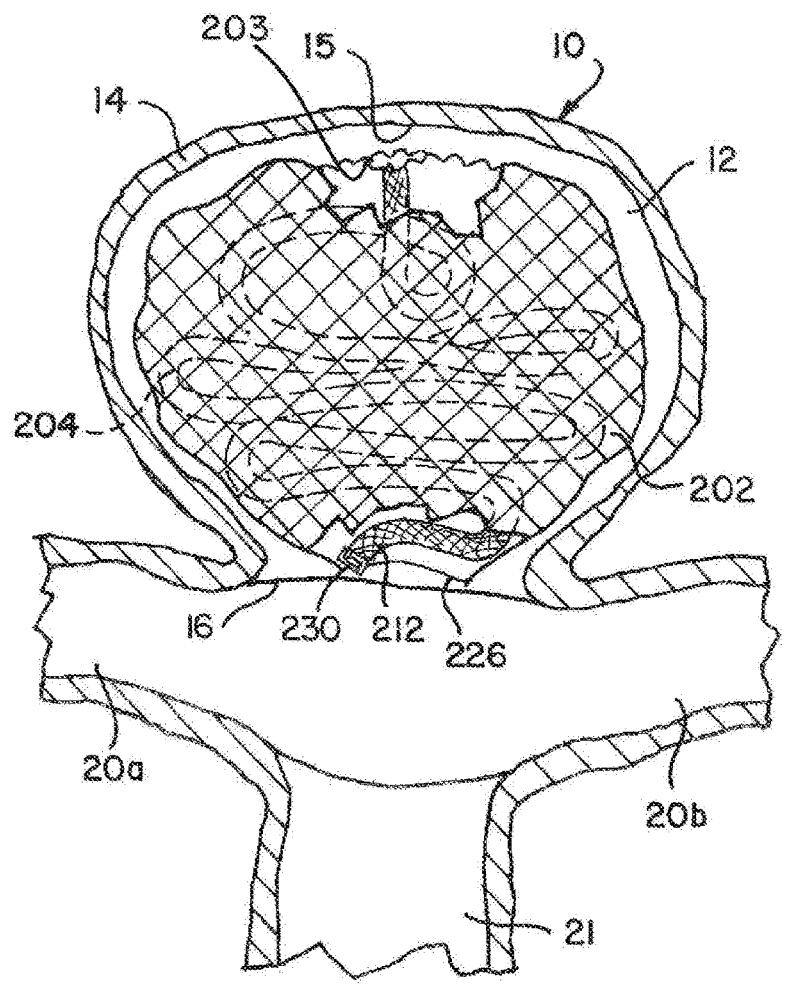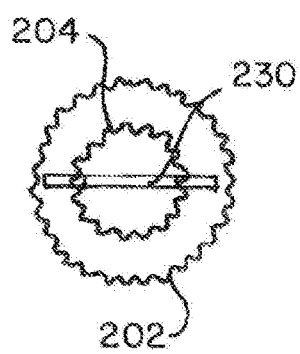

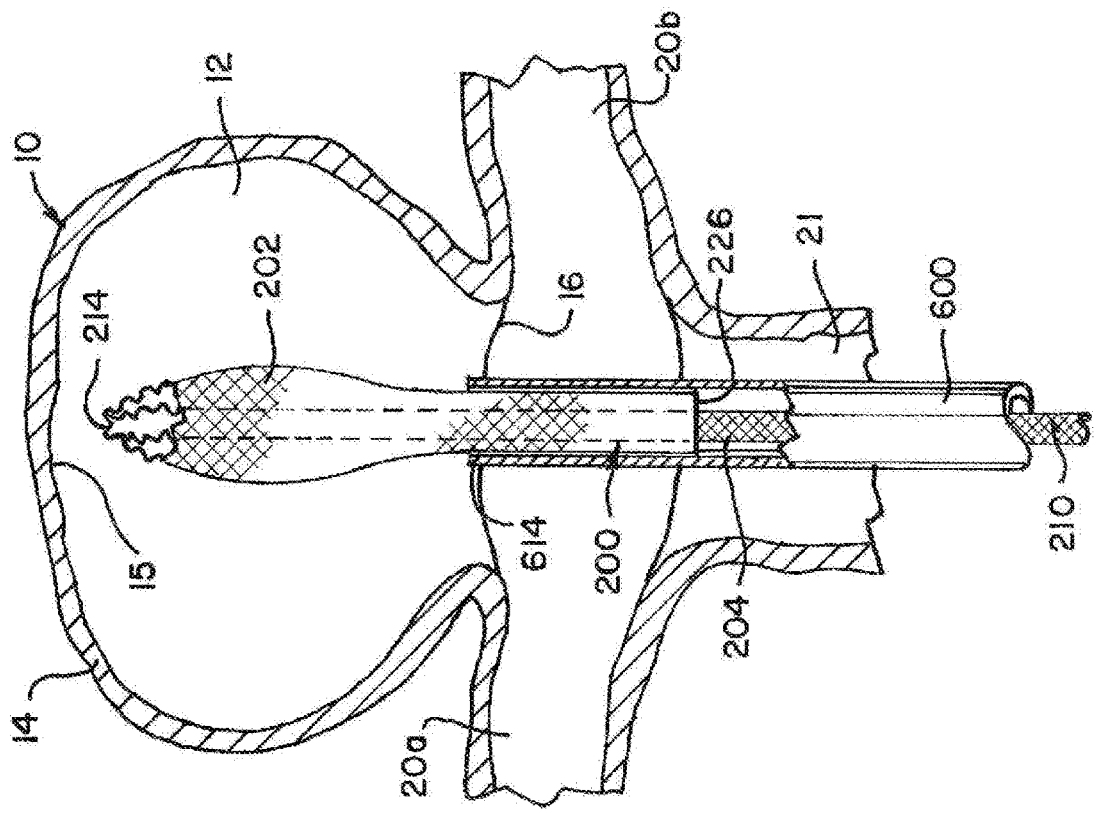
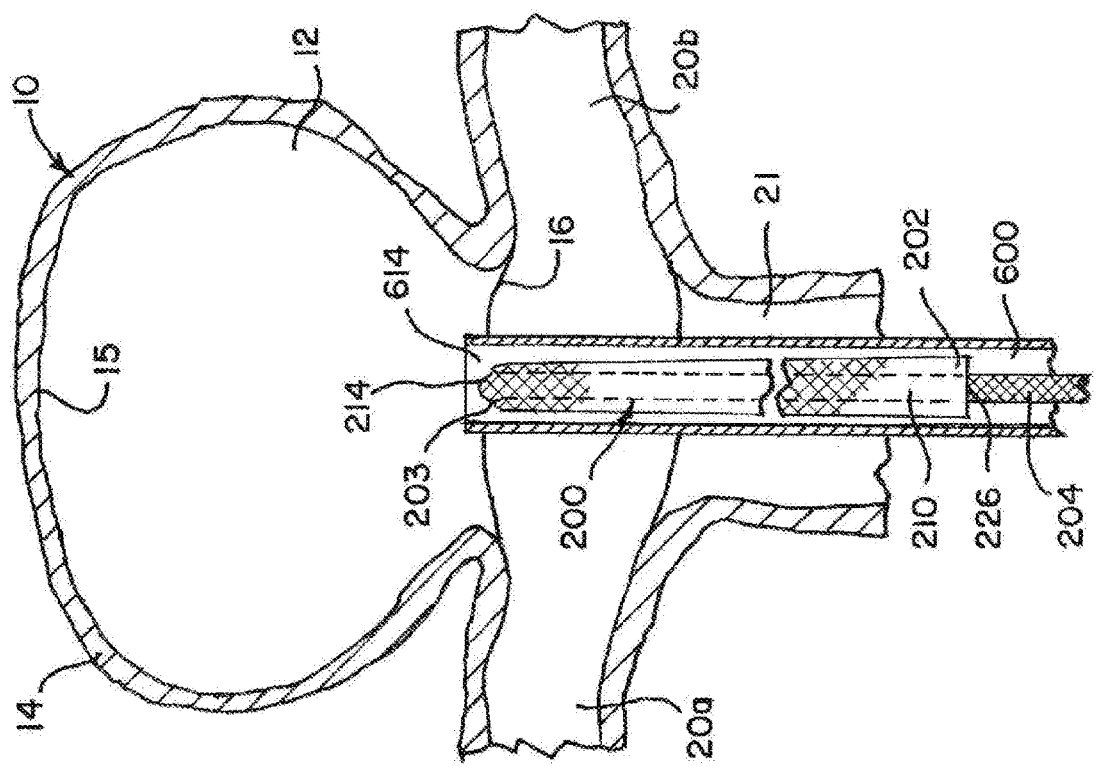

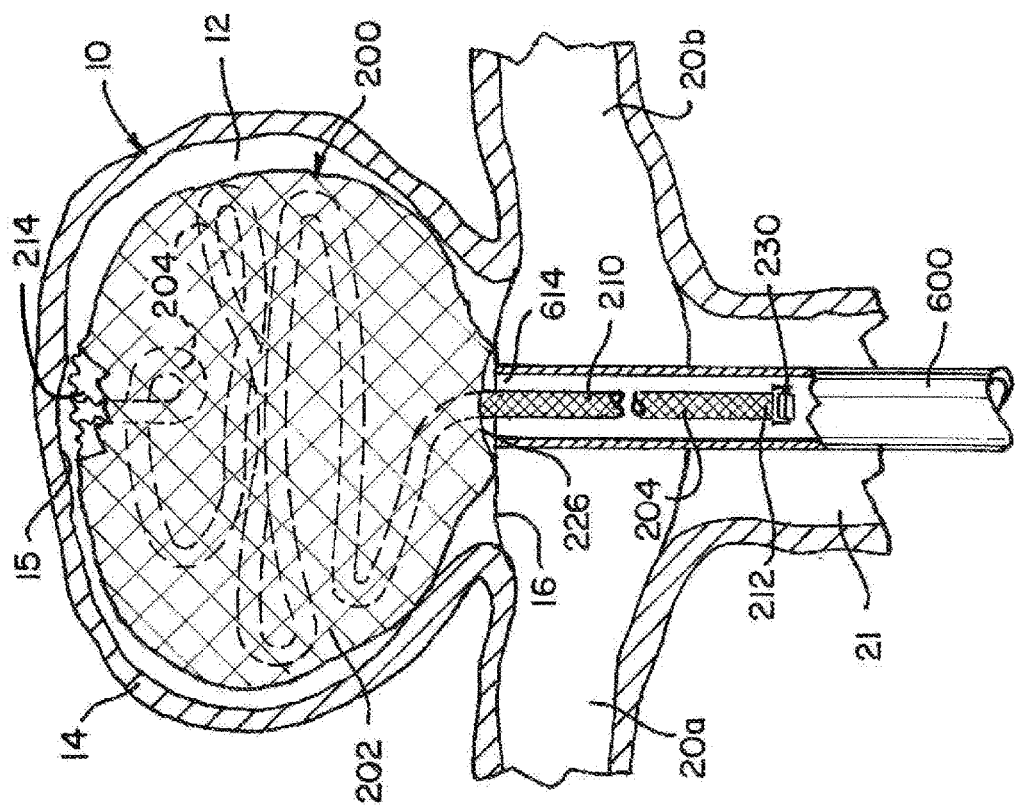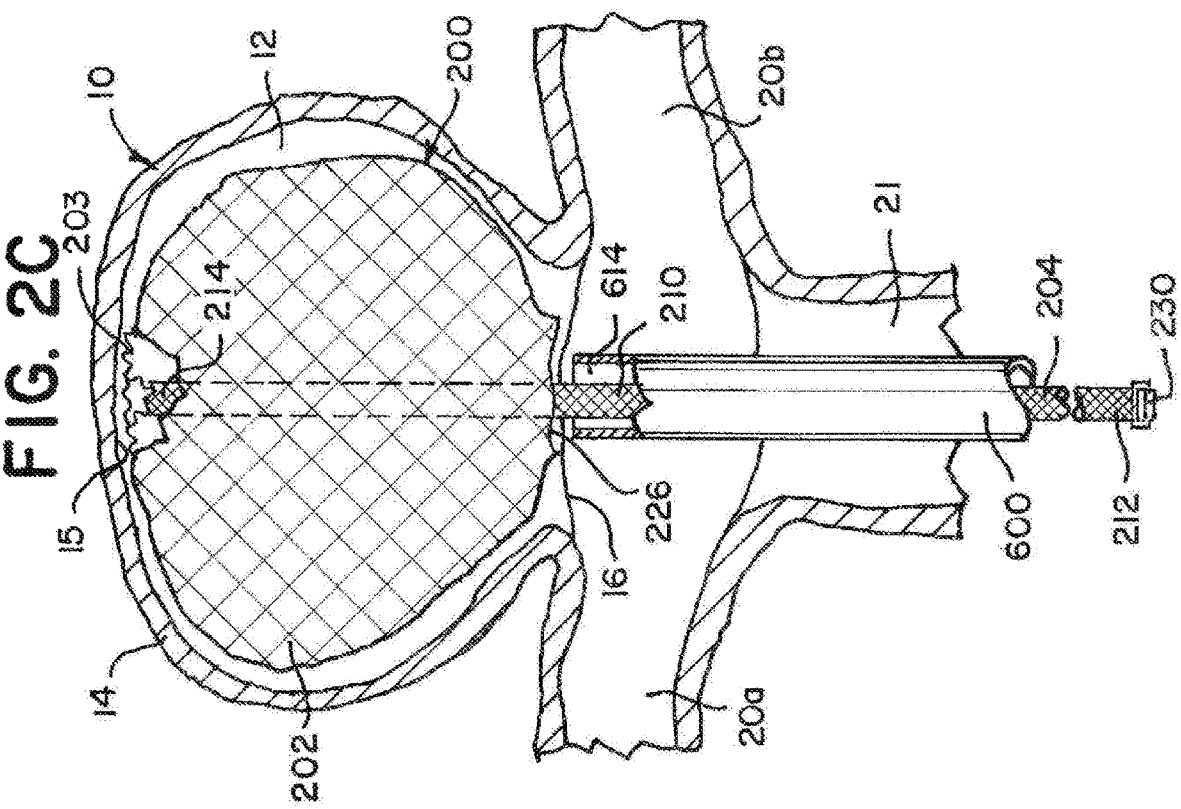

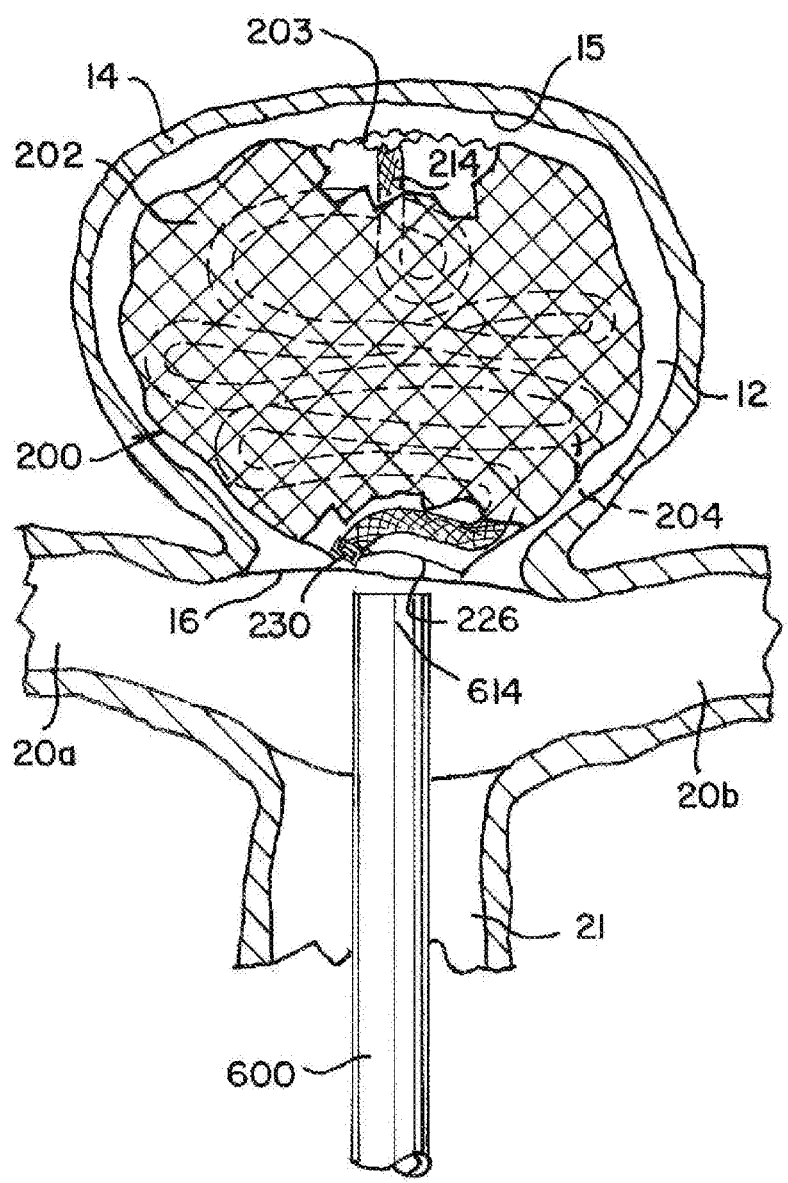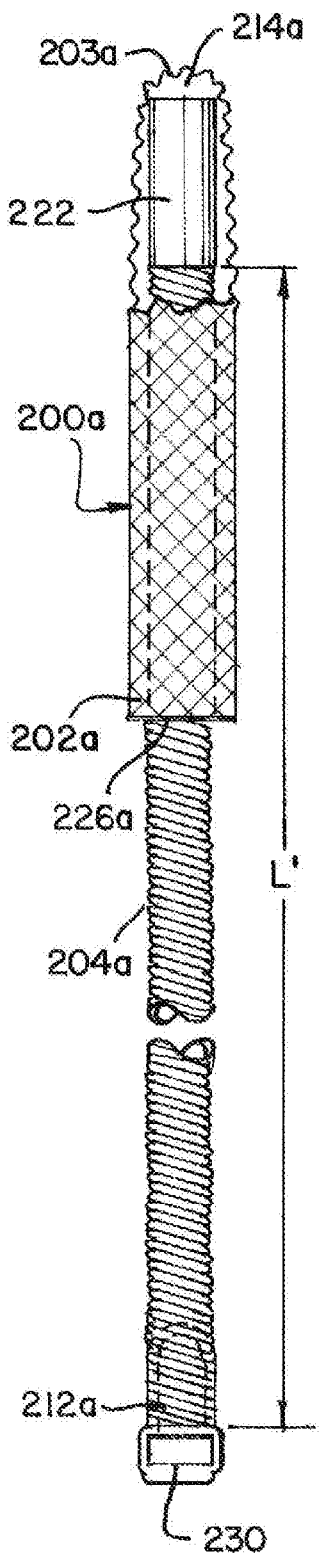

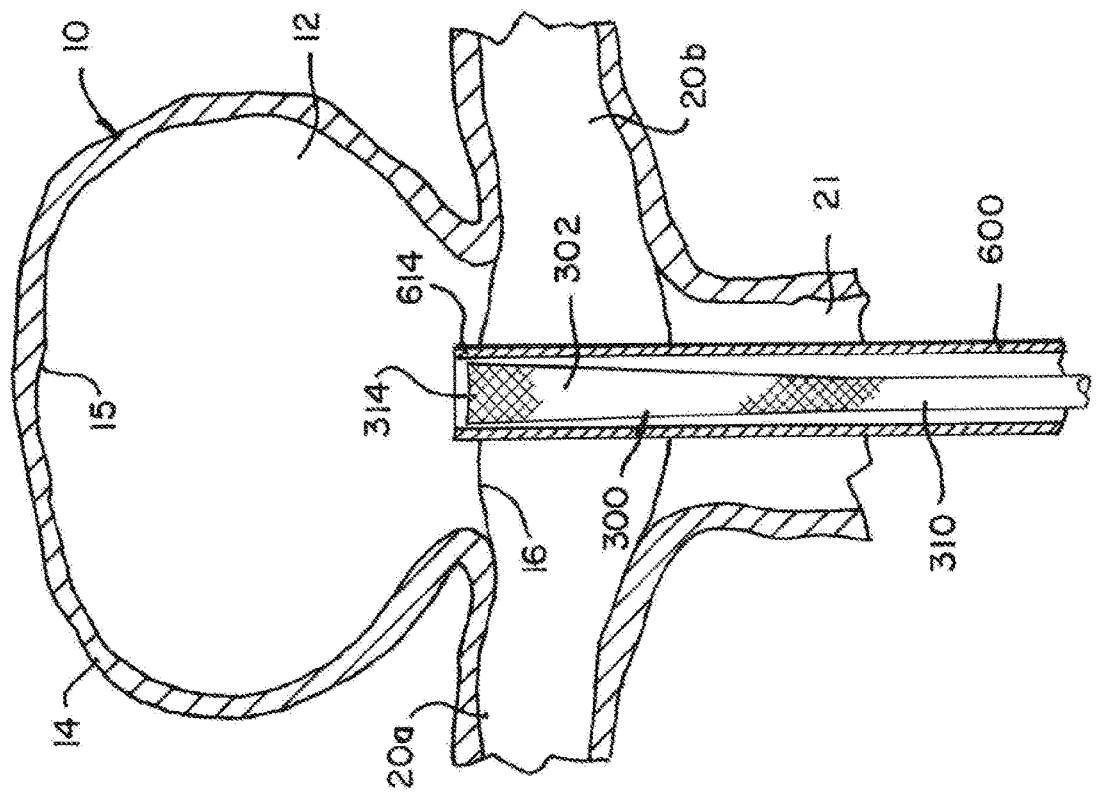
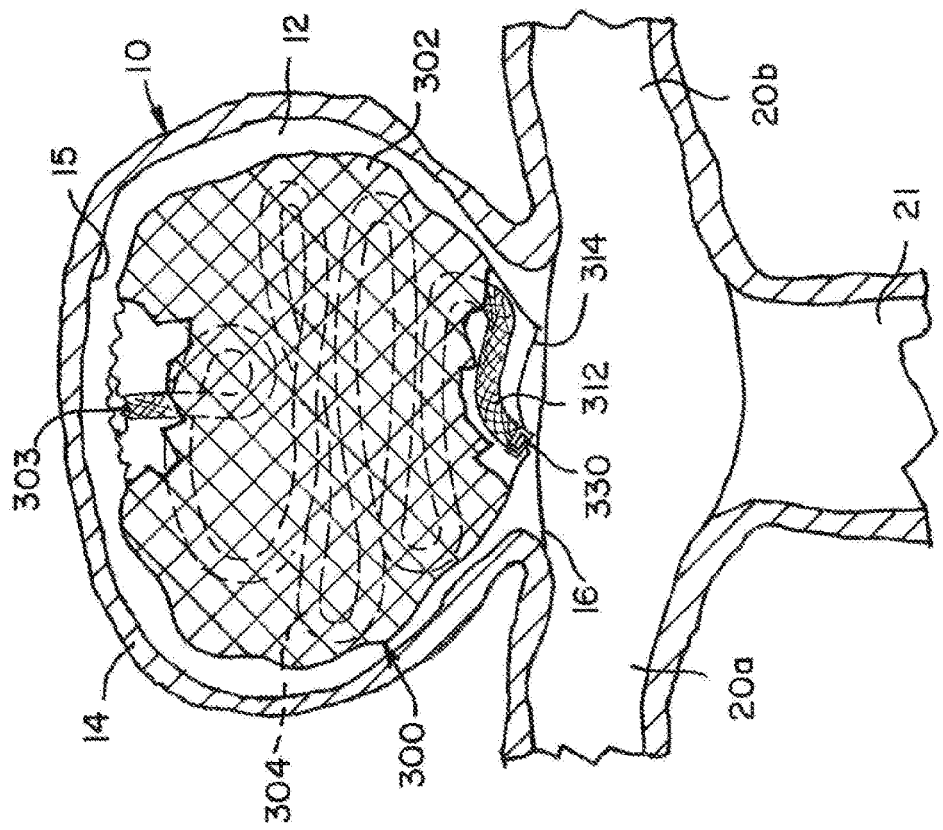

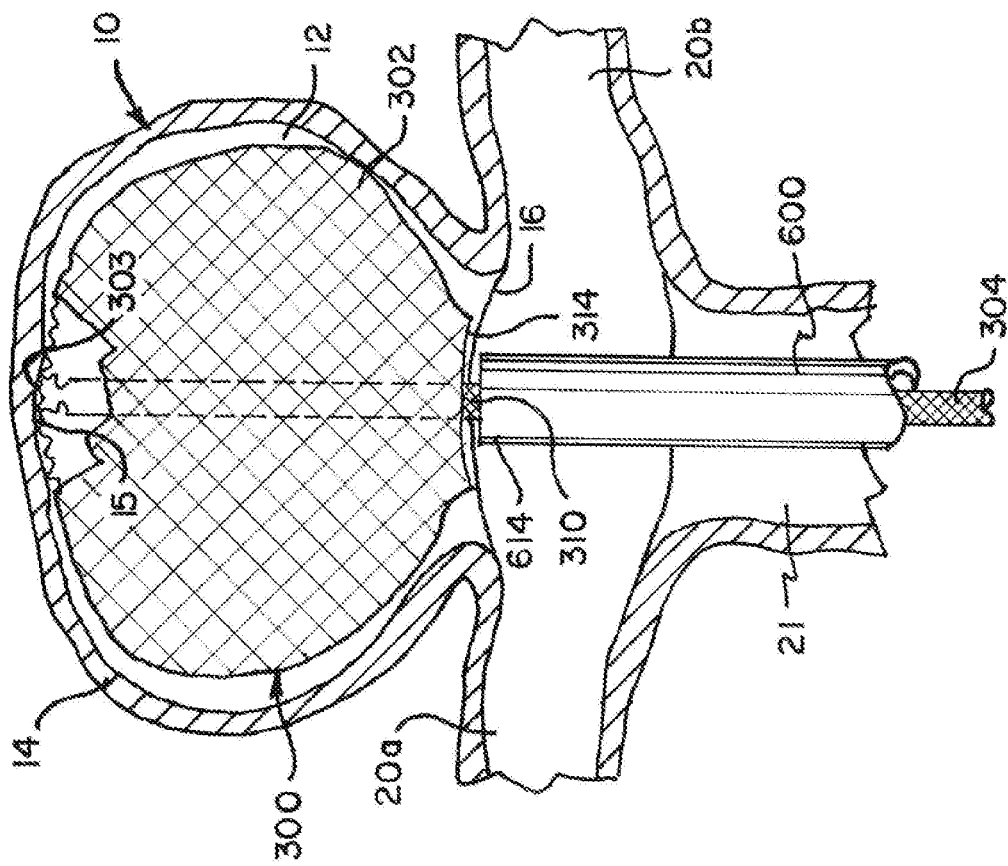
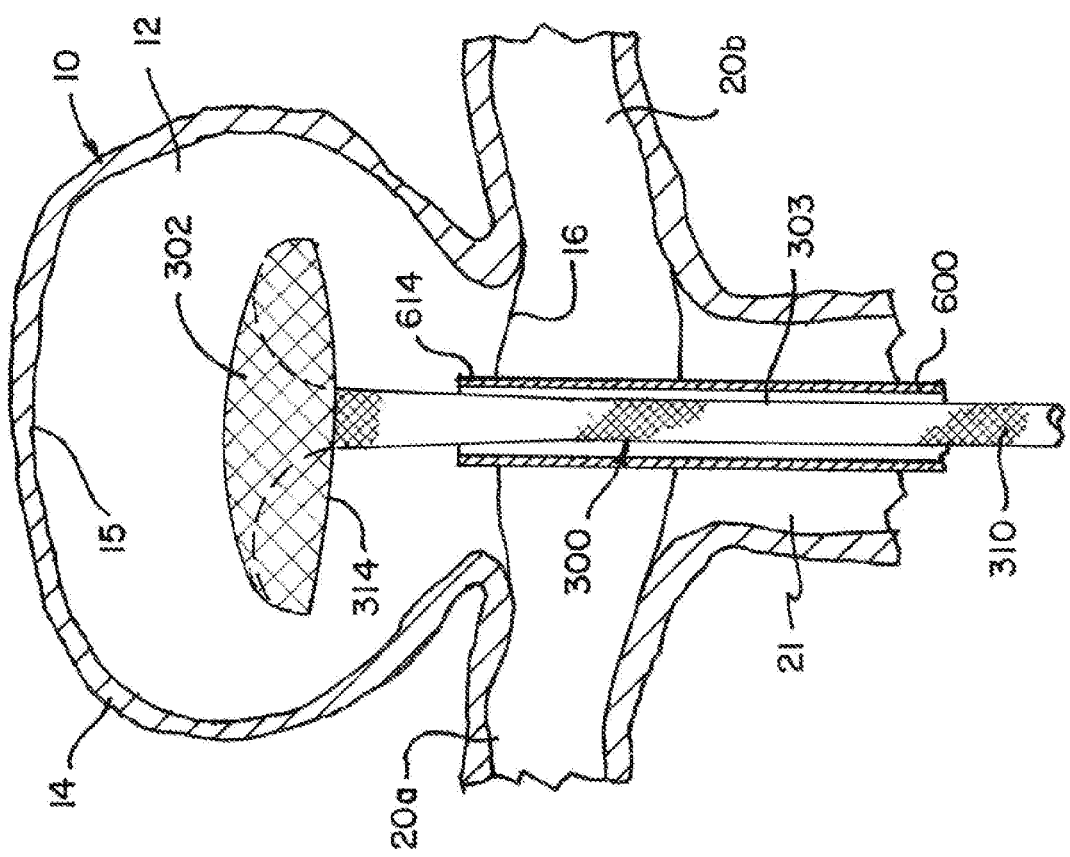

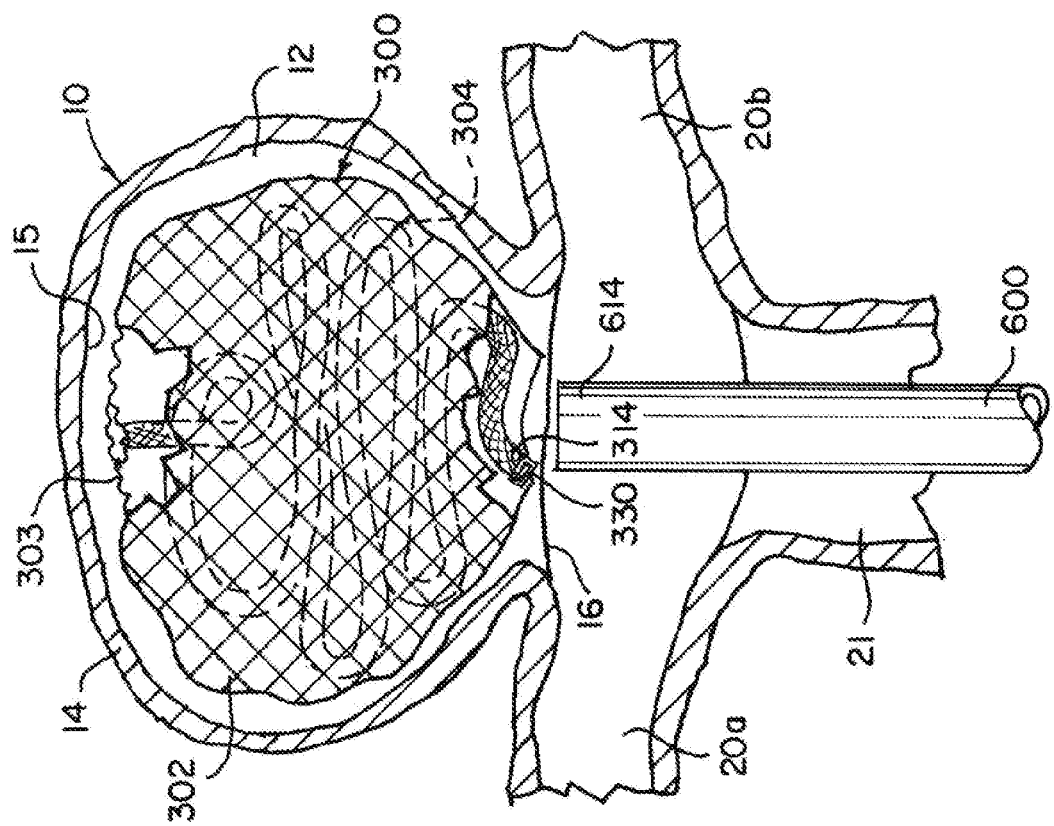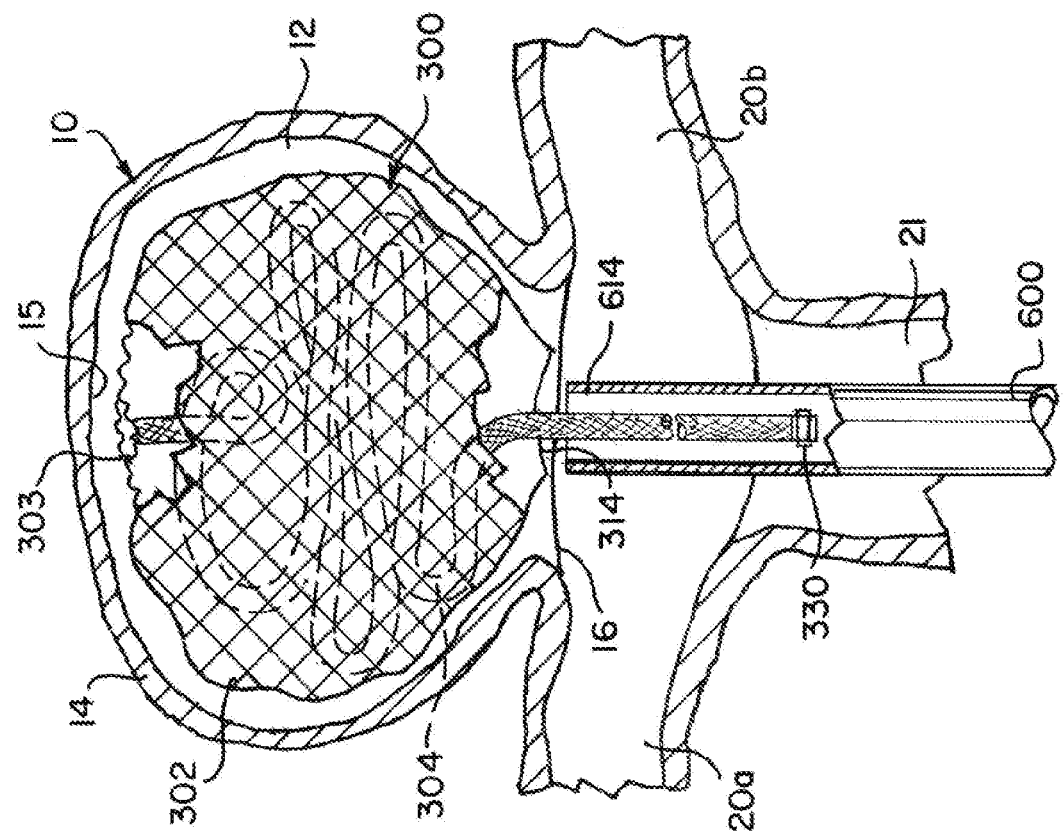

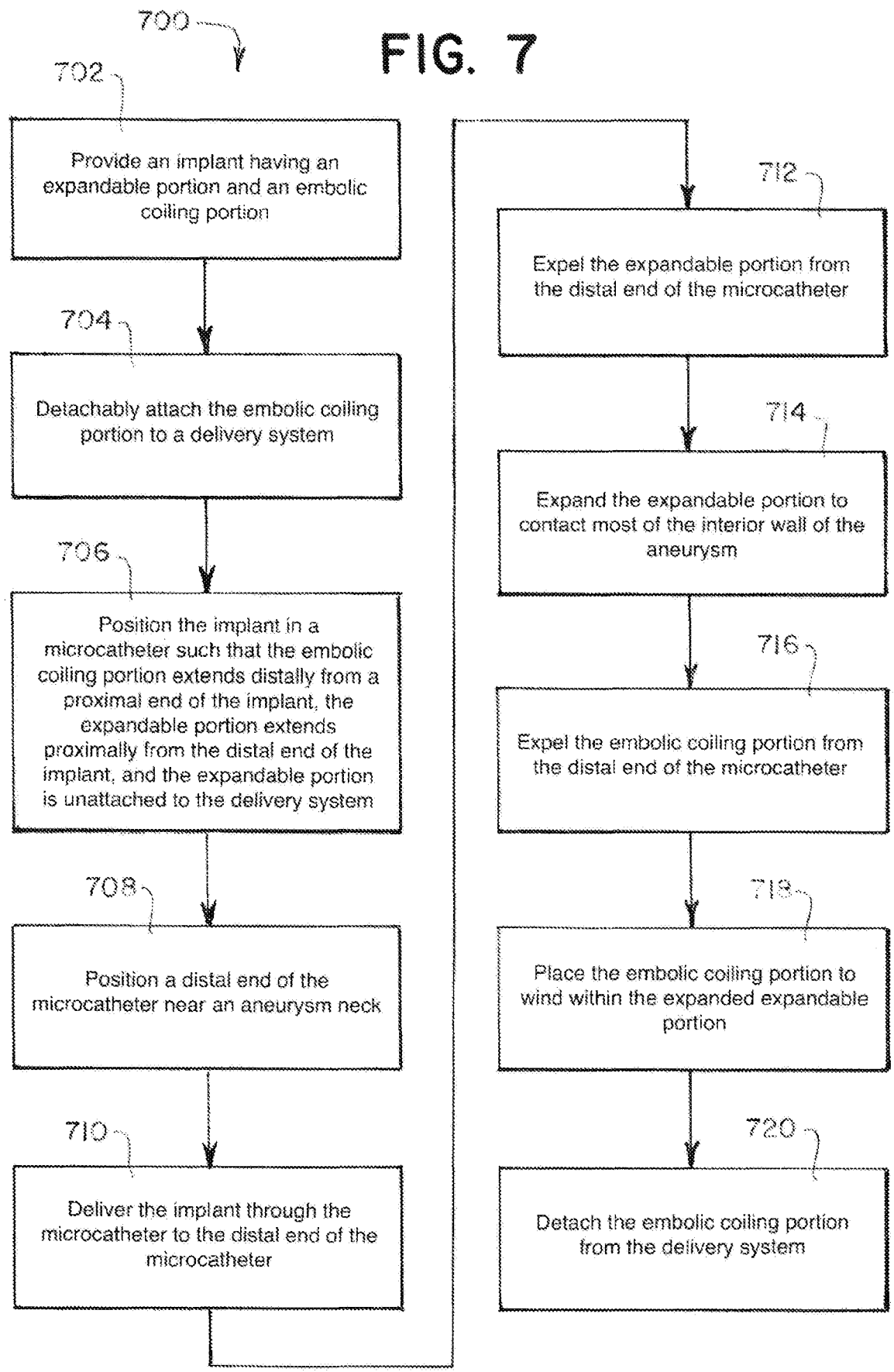

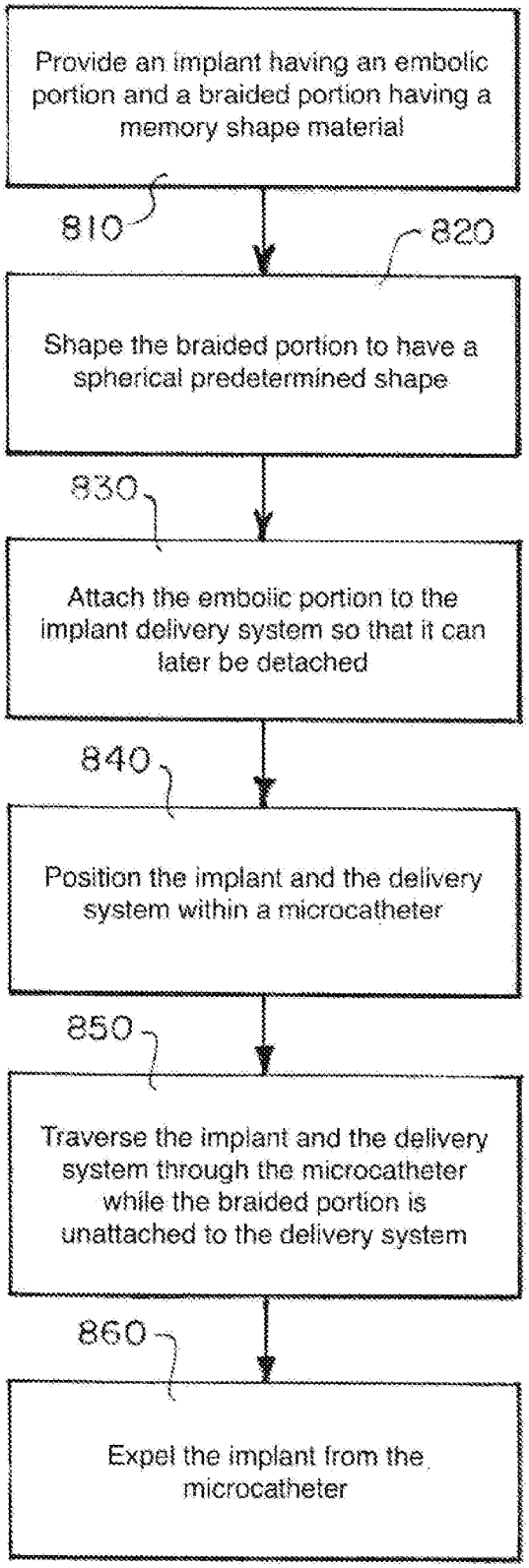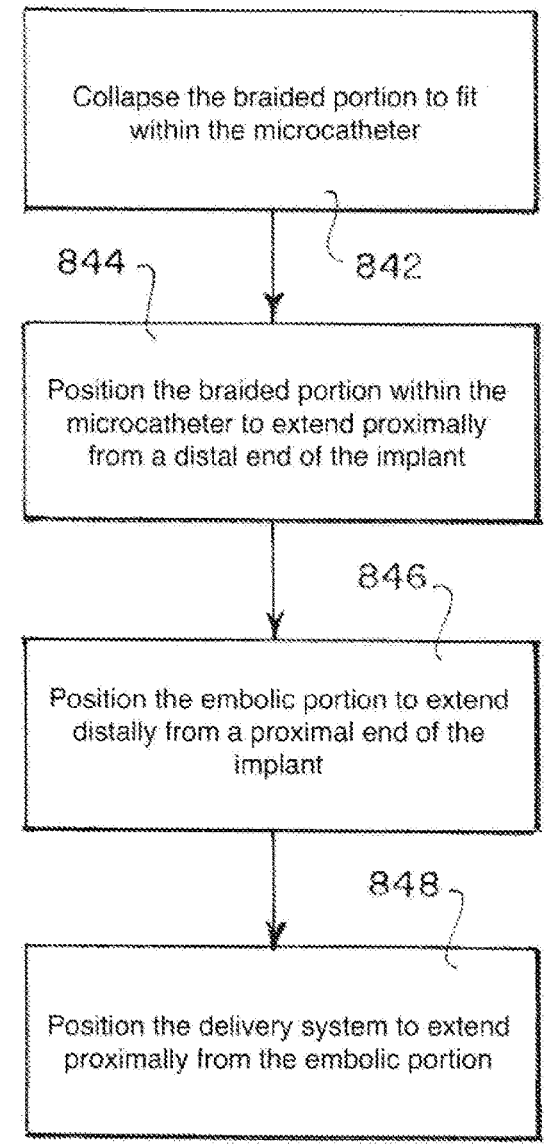

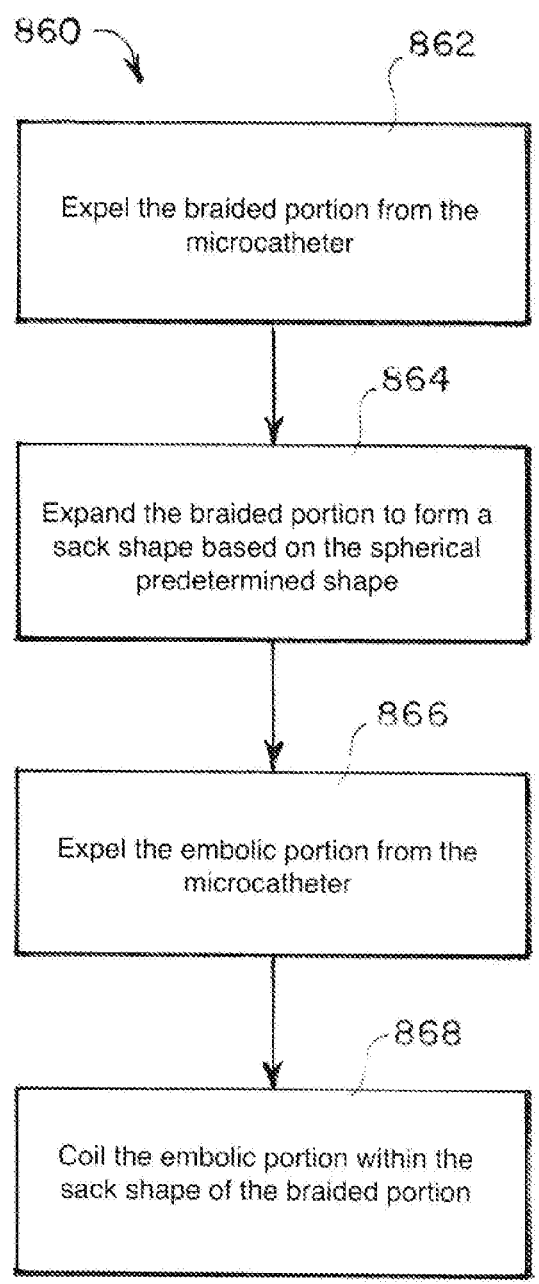

ANEURYSM TREATMENT DEVICE

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that either fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance. Naturally formed thrombotic masses formed by treating the entrance of the aneurysm with embolic coils can improve healing compared to aneurysm masses packed with embolic coils by reducing possible distention from arterial walls and permitting reintegration into the original parent vessel shape along the neck plane. However, embolic coils delivered to the neck of the aneurysm can potentially have the adverse effect of impeding the flow of blood in the adjoining blood vessel; at the same time, if the entrance is insufficiently packed, blood flow can persist into the aneurysm. Treating certain aneurysm morphology (e.g. wide neck, bifurcation, etc.) can required ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, because of flow, or large aneurysm size.

Alternatives to embolic coils are being explored, for example a tubular braided implant is disclosed in US Patent Publication Number 20180242979, incorporated herein by reference. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants.

There is therefore a need for improved methods, devices, and systems for implants for aneurysm treatment.

SUMMARY

It is an object of the present invention to provide systems, devices, and methods to meet the above-stated needs. Generally, in examples herein, an implant having an elongated portion and an expandable braided sack portion can be delivered through a catheter and implanted in an aneurysm such that elongated portion loops within the braided sack and the braided sack at least partially occludes the aneurysm neck.

An example implant can include an expandable braided sack portion, an elongated looping portion joined to the braided sack portion, and a detachment feature joined to the elongated looping portion. The implant can move from a delivery configuration to an implanted configuration. In the delivery configuration, the implant can be sized to be delivered through a lumen of a catheter to a treatment site, and in the implanted configuration, the implant can be sized to secure within an aneurysm. In the delivery configuration, the expandable braided sack portion can extend from a distal end of the implant, the elongated looping portion can extend proximally from the expandable braided sack portion, the detachment feature can be positioned near a proximal end of the implant, and the detachment feature can be detachably attached to a delivery system.

The expandable braided sack portion can be unattached to the delivery system when the implant is in the delivery configuration, in the implanted configuration, and throughout the transition from the delivery configuration to the implanted configuration during treatment of an aneurysm. In the implanted configuration, the expandable braided sack portion can be sized to contact a majority of an interior wall of the aneurysm, can contain the elongated looping portion, and can occlude some or all of the opening of the neck of the aneurysm. The expandable braided sack portion can have a free end, and in the implanted configuration, the free open end can be positioned at the aneurysm neck. In the implanted configuration the elongated looping portion can wind within the expandable braided sack portion.

In the delivery configuration the implant can have a fold at its' distal end, the expandable braided sack portion can encompass some of the elongated looping portion, and the free open end of the expandable braided sack portion can encircle the elongated looping portion. In the implanted configuration, a fold can define a boundary between the elongated looping portion and the expandable braided sack portion, and the fold can be positioned along a distal surface of the interior aneurysm wall. The fold at the distal end of the implant in the delivery configuration can be the same fold positioned along the distal surface of the aneurysm wall in the implanted configuration.

Alternatively, in the delivery configuration, the free open end can be positioned at the distal end of the implant and the implant can extend from the free open end at the distal end of the implant to the detachment feature at the proximal end of the implant. When the implant configured thusly, exits a catheter and the braided sack portion enters the aneurysm, a fold can form, and the fold can be positioned along a distal surface of the interior aneurysm wall.

The elongated looping portion and the expandable braided sack portion can be portions of a contiguous tubular braid. A fold can define a boundary between the elongated looping portion and the expandable braided sack portion, and the elongated looping portion can have a length measurable from the fold to the detachment feature. The elongated looping portion of the contiguous tubular braid can have a substantially uniform circumference along most of its length Alternatively, the elongated looping portion can have an embolic coil and the expandable braided sack portion can be a tubular braid.

When the implant is implanted and left in an aneurysm at the completion of an aneurysm treatment, the implant can include only the sack portion, the elongated looping portion, and the detachment feature. The implant need not have any other features such as additional detachment features or anchoring elements.

An example method of treating an aneurysm can include one or more of the following steps presented in no particular order, and the method can include additional steps not included here. An implant having an expandable portion and an embolic coiling portion can be provided. The embolic coiling portion can be detachably attached to a delivery system. The implant can be positioned within a microcatheter such that the embolic coiling portion extends distally from a proximal end of the implant, the expandable portion extends proximally from the distal end of the implant, and the expandable portion is unattached to the delivery system. The distal end of the microcatheter can be positioned near the aneurysm neck. The implant can be delivered through the microcatheter to the distal end of the microcatheter. The expandable portion can be expelled from the distal end of the microcatheter. The expandable portion can be expanded to contact a majority of the interior wall of the aneurysm. The embolic coiling portion can be expelled from the distal end of the microcatheter. The embolic coiling portion can be placed to wind within the expanded expandable portion. The embolic coiling portion can be detached from the delivery system.

When the implant is positioned in a microcatheter, a fold can be positioned at the distal end of the implant and the expandable portion can be positioned to encompass at least a portion of the embolic coiling portion. Alternatively, when the implant is positioned in a microcatheter, a free open end of the implant can be positioned at the distal end of the implant.

The expandable portion can be anchored to the interior wall of the aneurysm, and the expandable portion can be placed to inhibit the embolic coiling portion from exiting a sac of the aneurysm. The expandable portion can have a free open end, and the free open end can be positioned at the aneurysm neck. The implant can be folded to create a fold that defines a boundary between the expandable portion and the embolic coiling portion. The fold can be positioned near a distal surface of the interior aneurysm wall.

When the implant having the expandable portion and the embolic portion is provided, a contiguous tubular braid can be provided, and the expandable portion and the embolic portion can be portions of the contiguous tubular braid. When the embolic coiling portion of the contiguous braid is placed to wind within the expanded expandable portion, a substantially uniform circumference can be maintained along most of the length of the embolic coiling portion. Alternatively, when the implant having the expandable portion and the embolic portion is provided, a tubular braid joined an embolic coil can be provided such that the tubular braid includes the expandable portion and the embolic coil includes the embolic portion.

A detachment feature can be provided and affixed to the embolic coiling portion. The detachment feature can be detachably attached to the delivery system. To implant the expandable portion, embolic coiling portion, and the detachment feature in the aneurysm, the detachment feature can be detached from the delivery system. When the detachment feature is detached, only the expandable portion, embolic coiling portion, and the detachment feature can remain implanted in the implant.

Another example method for treating an aneurysm can include one or more of the following steps presented in no particular order, and the method can include additional steps not included here. An implant can be provided having a braided portion and an embolic portion. The braided portion can include a memory shape material and can have a spherical or globular predetermined shape. The embolic portion can be detachably attached to an implant delivery system. The implant and the delivery system can be positioned within a lumen of a microcatheter. When the implant and the delivery system is positioned in the microcatheter, the braided portion can be collapsed to fit in the lumen and positioned in the lumen to extend proximally from the distal end of the implant, the embolic portion can be positioned to extend distally from the proximal end of the implant, and the delivery system can be positioned to extend proximally from the embolic portion. The implant and the delivery system can traverse through the lumen of the microcatheter while the braided portion is unattached to the delivery system. The implant can be expelled from the microcatheter. When the implant is expelled, the braided portion can be expelled from the microcatheter and expanded to form a sack shape based on the spherical predetermined shape, the embolic portion can be expelled from the microcatheter and coiled within the sack shape of the braided portion. When the implant is expelled, an opening can be positioned in the sack shape of the braided portion can be positioned near the aneurysm neck, a fold can be positioned to define a boundary between the braided portion and the embolic portion near a distal surface of the aneurysm wall, and the embolic portion can traverse through the opening in the sack shape.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1A through 1C are illustrations of an example implant in a collapsed or delivery configuration (FIG. 1A), a cross section of the collapsed implant of FIG. 1A (FIG. 1C), and the example implant in an implanted or expanded configuration (FIG. 1B) according to aspects of the present invention;

FIGS. 2A through 2E are illustrations of an example implant during implantation steps according to aspects of the present invention;

FIGS. 3A and 3B are illustrations of an example implant in a collapsed or delivery configuration (FIG. 3A) and in an implanted or expanded configuration (FIG. 3B) according to aspects of the present invention;

FIGS. 4A and 4B are illustrations of an example implant in a collapsed or delivery configuration (FIG. 4A) and in an implanted or expanded configuration (FIG. 4B) according to aspects of the present invention;

FIGS. 5A through 5E are illustrations of an example implant during implantation steps according to aspects of the present invention;

FIGS. 7 through 10 are flow diagrams outlining example method steps for treating an aneurysm according to aspects of the present invention.

DETAILED DESCRIPTION

Figure 3B:
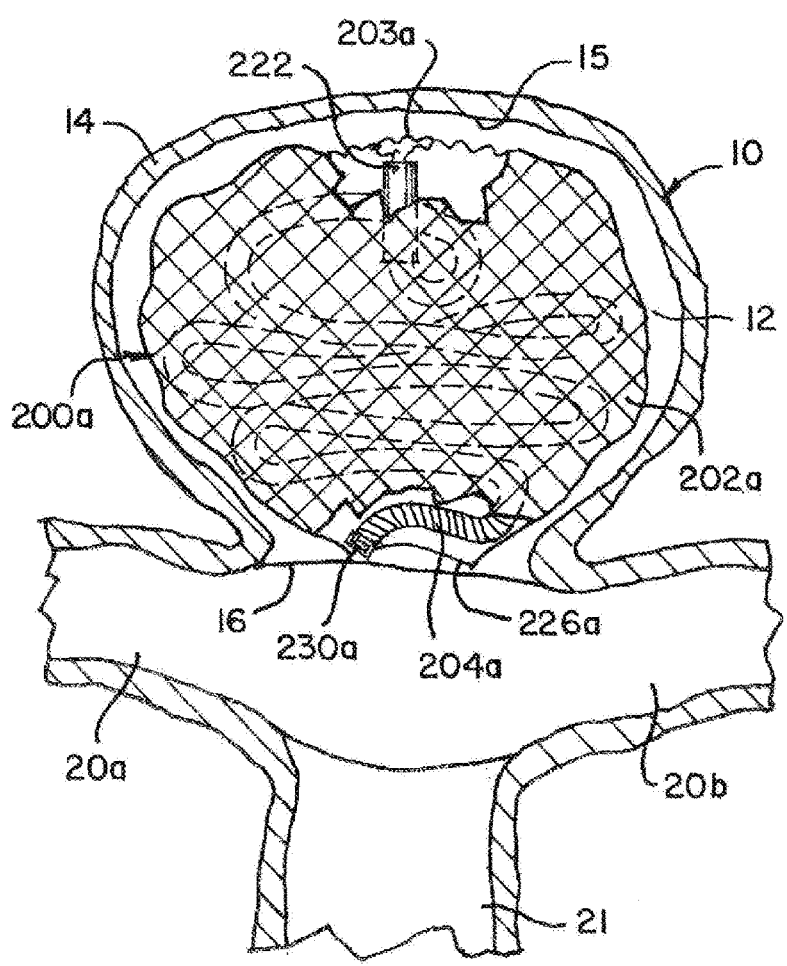

As object of the present invention is to provide an embolic implant suitable for endovascular treatment of an aneurysm in a patient. The implant can have two parts that can reshape upon delivery to a treatment site.

FIG. 1A illustrates an example implant 200 in a collapsed or delivery configuration. In the delivery configuration, the implant 200 can be sized to be delivered to a treatment site through a catheter inserted in vasculature of a patient. FIG. 1C illustrates a cross sectional view of the collapsed implant 200 as indicated in FIG. 1A. FIG. 1B illustrates the example implant 200 illustrated in FIG. 1A in an expanded or implanted configuration. In the implanted configuration, the implant 200 can be positioned in a sac 12 of an aneurysm 10 to divert blood flow from a neck 16 of the aneurysm 10 and fill the sac 12 with embolic material. The embolic material in the aneurysm sac 12 can promote the formation of a thrombotic mass in the aneurysm 10, and the diversion of blood flow from the aneurysm neck 16 can induce venous stasis in the aneurysm and reduce the likelihood that the aneurysm recanalizes after an aneurysm treatment procedure.

Referring collectively to FIGS. 1A through 1C, the implant 100 can include an elongated portion 204, an expandable sack portion 202, and a detachment feature 230. The elongated portion 204 and the expandable sack portion 202 can each be braided. The expandable sack portion 202 and elongated portion 204 can be manufactured as two separate structures or as a contiguous braided structure. Braided portions can be made from braided Nitinol, cobalt, chromium, plastic, or other suitable material. Portions of the implant 200 can be made from a memory shape material having a predetermined shape and a deformed shape. The memory shape material can be in the deformed shape when the implant 200 is in the delivery configuration and can move toward the predetermined shape when the implant 200 is in the expanded or implanted configuration. When implanted, the memory shape material can be restricted by anatomical geometries and the memory shape material can take a shape that approaches the predetermined shape but does not match the predetermined shape due to the anatomical restrictions.

The detachment feature 230 can be joined to the elongated portion 204, and the detachment feature 230 can be detachably attached to a delivery system when the implant 200 is delivered through a catheter to a treatment site.

Referring to FIG. 1A, in the delivery configuration, the detachment feature 230 can be positioned at the proximal end 212 of the implant 200, the elongated portion 204 can extend distally from the detachment feature 230 to a fold 203 positioned at a distal end 214 of the implant 200, and the expandable braided sack portion 202 can extend proximally from the fold 203. In the delivery configuration, the expandable braided sack portion 202 can extend distally from the fold 203 to wrap around a part of the length L of the elongated portion 204, and the expandable braided sack portion 202 can have an open end 226 that circles the elongated portion 204. The open end 226 is preferably simply the open end of a braid without any ancillary attachments. The open end 226 need not be attached to a delivery system as the implant 200 is delivered through a catheter to the treatment site or as the implant 200 is deployed within the aneurysm. Strands of the braid 210 at the open end 226 can be free, cut ends; or, alternatively, the strands at the open end 226 be closed, meaning strands within the braid at the open end are attached to each other by glue, weld, etc. or the strands bend back at the open end. Free cut ends can have an advantage of being easier to manufacture while the closed ends can have an advantage of being more atraumatic compared to the cut ends.

Referring to FIGS. 1A and 1B, the implant 200 can include memory shape material and can be pre-shaped such that the expandable braided sack portion 202 forms a globular or spherical shape and a fold 203 separates the elongated looping portion 204 from the expandable braided sack portion 202. The memory shape material can be heat set into the predetermined shape. The spherical shape, fold 203, and the loops of the elongated portion can be shaped by heat setting. The implanted shape illustrated in FIG. 1B can be based on the predetermined shape and the shape of the interior wall 14 of the aneurysm 10. To collapse the implant from the predetermined shape so that it can be delivered through a catheter, the elongated looping portion 204 can be extended and straightened and the sack portion 202 can be compressed around the elongated looping portion 204. The fold created when the implant was pre-shaped can be further folded to define a boundary between the sack portion 202 and the elongated looping portion 204 when the implant 200 is in the delivery configuration.

Referring to FIG. 1B, in the implanted configuration, the expandable braided sack portion 202 can expand to contact a majority of the interior wall 14 of the aneurysm 10. The fold 203 can be positioned near a distal surface 15 of the aneurysm wall 14. The elongated portion 204 can wind within the aneurysm sac 12 and within the braided sack portion 202. By anchoring within the sac 12, the expandable braided sack portion 202 can maintain proper positioning of the implant 200 in the aneurysm 10 and prevent portions of the implant 200, such as the elongated portion 204, from extending into a blood vessel 20a, 20b, 21 or exiting the aneurysm sac 12.

The free open end 226 of the expandable braided sack portion 202 can define an opening in the sack when the implant is in the implanted or pre-shaped configuration, and when implanted, the opening can be positioned near the aneurysm neck 16. The opening can be sized such that a portion of the expandable braided sack portion 202 extends across the aneurysm neck 16 to occlude the neck. The elongated portion 204 can enter the aneurysm sac 12 and the sack of the expandable braided sack portion 202 through the opening. The elongated portion 204 can wind or loop around in a complex coiled shape within the expandable braided sack portion 202 and within the aneurysm sac 12. The looped elongated portion 204 can press against the braided sack 202 and provide a force against an interior surface of the braided sack 202 to press an exterior surface of the braided sack 202 to the aneurysm wall 14 to further secure the anchoring of the braided sack 202 within the aneurysm sac 12.

The looped elongated portion 204 can fill a majority of the aneurysm sac 12. The implanted braided sack 202 can be a braided mesh with a porosity sized to inhibit blood flow into the aneurysm 10. The elongated portion can have a substantially uniform circumference 206 along much or all of its length L, and it can maintain the substantially uniform circumference 206 as it moves from the delivery configuration to the implanted configuration.

FIGS. 2A through 2E are illustrations of an example implant during implantation steps. FIG. 2A illustrates an implant 200 positioned within a catheter 600 near an aneurysm 10. The aneurysm 10 is illustrated positioned at a bifurcated blood vessel having a stem vessel 21, a first side branch vessel 20a, and a second side blood vessel 20b. The catheter 600 can approach the aneurysm 10 from the stem vessel 21. It is contemplated that example implants 200 disclosed herein can be used for treating sidewall vessels according to methods described herein and as would be understood by a person of ordinary skill in the art. At the instant illustrated in FIG. 2A, the implant 200 is collapsed in the catheter 600. The implant 200 can include memory shape material that is in a deformed shape while it is collapsed in the catheter 600.

FIG. 2B illustrates the implant 200 during implantation. The implant 200 can include an expandable braided sack portion 202 and an elongated embolic portion 204. As the implant 200 is translated distally through the catheter 600, a fold 203 can be positioned at a distal end 214 of the implant 200, and the expandable braided sack portion 202 and the elongated looping portion 204 can extend proximally from the fold 203. Configured thusly, the braided sack portion 202 can be oriented in the catheter 600 so that when the implant 200 is pushed distally out of the catheter 600, the braided sack portion 202 is pushed out of the catheter 600 and into the sac 12 before a majority of the elongated looping portion 204 is begins to exit the catheter 600.

FIG. 2C illustrates the implant 200 after the braided sack portion 202 has exited the catheter 600 and expanded within the aneurysm 12. The braided sack portion 202 can expand to contact all or a majority of the interior wall 14 of the aneurysm 10. The braided sack 202 can expand toward the predetermined shape upon exiting the catheter 600. Contact with warm bodily fluid can cause the memory shape material in the braided sack 202 to move to the predetermined shape. The free open end 226 can define an opening in the braided sack 202, and the opening can be positioned at the aneurysm neck 16.

A fold 203 defining a boundary between the expanded braided sack 202 and the elongated portion 204 can be positioned near a distal surface 15 of the aneurysm wall 14. At the stage of implantation illustrated in FIG. 2C, the elongated portion 204 can extend from the fold 203, through the opening in the braided sack 202, and into the catheter 600.

FIG. 2D illustrates the elongated portion 204 exiting the catheter 600, entering the braided sack portion 202 through the free open end 226, and winding within the sack 202. As the elongated portion 204 exits the catheter 600, the elongated portion 204 can maintain its circumference 206 as it exits the catheter 600. The elongated portion 204 can wind or loop within the aneurysm sac 12 in response to contacting an interior surface of the expanded braided sack 202. Additionally, or alternatively, the elongated portion 204 can include memory shape material having a predetermined shape and a deformed shape. The predetermined shape can be a complex looped shape, and the deformed shape can be substantially straight. The elongated portion 204 can wind or loop within the aneurysm sac 12 in response to the memory shape material moving from the deformed shape toward the predetermined shape as the elongated portion 204 contacts blood as it exits the catheter 600. Additionally, or alternatively, the elongated portion 204 can include a flexible elastically deformable material having a relaxed shape that is a looped shape. The flexible elastically deformable material can be uncoiled to a substantially straight strand during delivery through a catheter and can collapse into the looped shape upon exiting the catheter 12.

At the instant illustrated in FIG. 2D the detachment feature 230 can remain attached to a delivery system. While the implant 200 is attached to the delivery system, the delivery system can be pulled proximally to withdraw all or portions of the implant 200. The delivery system can subsequently be pushed distally to reposition the implant 200.

FIG. 2E illustrates the implant 200 in a final implanted configuration such as described in relation to FIG. 1B. The detachment feature 230 can be moved distally by the delivery system past the plane of the aneurysm 16, through the open end 226 of the expanded sack portion 202, and into the aneurysm sac 12 prior to detachment from the delivery system. The elongated portion 204 can have a predetermined shape configured to facilitate the movement of the detachment feature 230 past the plane of the aneurysm neck 16 once the implant 200 is implanted. Additionally, or alternatively, the delivery system can be manipulated to place the detachment feature 230 within the sack portion 202. Once the implant 200 is implanted as illustrated in FIG. 2E, the delivery system can be detached and withdrawn, and the microcatheter 600 can be moved or extracted from the patient.

The open end 226 can remain open at the completion of the implantation, and the elongated portion 204, once secured within the sack 202, can be coiled near the opening defined by the open end 226 in such a way that blood flow is obstructed from entering the opening. In other words, sack 202 can occlude a portion of the neck 16 around the perimeter of the neck, and the elongated portion 204 can occlude the neck 16 at the opening in the sack 202 defined by the open end 226.

FIG. 3A illustrates an example implant 200a in a collapsed or delivery configuration. In the delivery configuration, the implant 200a can be collapsed to a size that can be delivered to a treatment site through a catheter inserted in vasculature of a patient. FIG. 3B illustrates the example implant 200a illustrated in FIG. 3A in an expanded or implanted configuration. In the implanted configuration, the implant 200a can be positioned in a sac 12 of an aneurysm 10 to divert blood flow from a neck 16 of the aneurysm 10 and fill the sac 12 with embolic material. The embolic material in the aneurysm sac 12 can promote the formation of a thrombotic mass in the aneurysm 10, and the diversion of blood flow from the aneurysm neck 16 can induce venous stasis in the aneurysm and reduce the likelihood that the aneurysm recanalizes after an aneurysm treatment procedure.

Comparing the example implant 200a illustrated in FIGS. 3A and 3B to the implant 200 illustrated in FIGS. 1A through 2E, the elongated portion 204a of the implant 200a in FIGS. 3A and 3B can be an embolic coil 204a rather than a braid 204 as illustrated in FIGS. 1A through 2E. The implant 200a illustrated in FIGS. 3A and 3B can be implanted following a procedure like that illustrated in FIGS. 2A through 2E.

Referring collectively to FIGS. 3A and 3B, the implant 200a can include the embolic coil 204a, an expandable braided sack portion 202a, a detachment feature 230a, and a connecting band 222 joining the embolic coil 204a to the expandable braid 202a. The connecting band 222 can include radiopaque material to facilitate visibility of the implant 200a under X-ray. The expandable braided sack portion 202a can be braided. Portions of the implant 200a, including the embolic coil 204a, can be made from a memory shape material having a predetermined shape and a deformed shape. The memory shape material can be in the deformed shape when the implant 200a is in the delivery configuration and can move toward the predetermined shape when the implant 200a is in the expanded or implanted configuration. When expanded or implanted, the memory shape material can be restricted by anatomical geometries and the memory shape material can take a shape that approaches the predetermined shape but does not match the predetermined shape due to the anatomical restrictions.

The detachment feature 230a can be joined to the elongated portion 204a, and the detachment feature 230a can be detachably attached to a delivery system when the implant 200a is delivered through a catheter to a treatment site.

Referring to FIG. 3A, in the delivery configuration, the detachment feature 230a can be positioned at the proximal end 212a of the implant 200a, the elongated portion 204 can extend distally from the detachment feature 230a to the connecting band 222, the braided portion 202a can have a fold 203a positioned at a distal end 214a of the implant 200a, and the expandable braided sack portion 202a can extend proximally from the fold 203a. In the delivery configuration, the expandable braided sack portion 202a can extend distally from the fold 203a to wrap around a part of the length L' of the embolic coil 204a, and the expandable braided sack portion 202a can have a free open end 226a that circles the embolic coil 204a. Strands of the braided portion 202a at the open end 226a can be free, cut ends; or, alternatively, the strands at the open end 226a be closed, meaning strands within the braid at the free open end 226a are attached to each other by glue, weld, etc. or the strands bend back at the open end 226a. Free cut ends can have an advantage of being easier to manufacture while the closed strand ends can have an advantage of being more atraumatic compared to the cut ends.

Referring to FIGS. 3A and 3B, the implant 200a can include memory shape material and can be pre-shaped such that the expandable braided sack portion 202a forms a globular or spherical shape and the braid can have a fold 203a near the connecting band 222. The memory shape material can be heat set into the predetermined shape. The implanted shape illustrated in FIG. 3B can be based on the predetermined shape and the shape of the interior wall 14 of the aneurysm 10. To collapse the implant from the predetermined shape so that it can be delivered through a catheter, the embolic coil 204a can be extended and straightened and the sack portion 202a can be compressed around the elongated looping portion 204a. The fold created when the implant was pre-shaped can be further folded and positioned at the distal end 214a of the implant 200a when the implant 200a is in the delivery configuration.

Referring to FIG. 3B, in the implanted configuration, the expandable braided sack portion 202a can expand to contact a majority of the interior wall 14 of the aneurysm 10. The fold 203a can be positioned near a distal surface 15 of the aneurysm wall 14. The embolic coil 204a can wind within the aneurysm sac 12 and within the braided sack portion 202a. By anchoring within the sac 12, the expandable braided sack portion 202a can maintain proper positioning of the implant 200a in the aneurysm 10 and prevent portions of the implant 200a, such as the embolic coil 204a, from extending into a blood vessel 20a, 20b, 21 or exiting the aneurysm sac 12.

The free end 226a of the expandable braided sack portion 202a can define an opening in the sack when the implant 200a is in the implanted or pre-shaped configuration, and when implanted, the opening can be positioned near the aneurysm neck 16. The opening can be sized such that a portion of the expandable braided sack portion 202a extends across the aneurysm neck 16 to occlude the neck. The embolic coil 204a can enter the aneurysm sac 12 and the sack of the expandable braided sack portion 202a through the opening. The elongated portion 204a can wind or loop around in a complex coiled shape within the expandable braided sack portion 202a and within the aneurysm sac 12.

The looped elongated portion 204a can press against the braided sack 202a and provide a force against an interior surface of the braided sack 202a to press an exterior surface of the braided sack 202a to the aneurysm wall 14 to further secure the anchoring of the braided sack 202a within the aneurysm sac 12.

The looped embolic coil 204a can fill a majority of the aneurysm sac 12. The implanted braided sack 202a can be a braided mesh with a porosity sized to inhibit blood flow into the aneurysm 10.

Figure 4A:
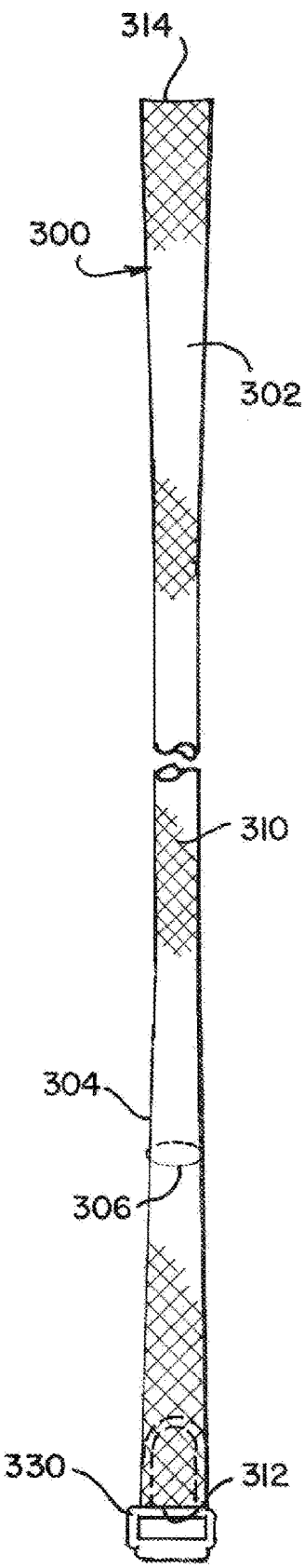
Figure 6A:
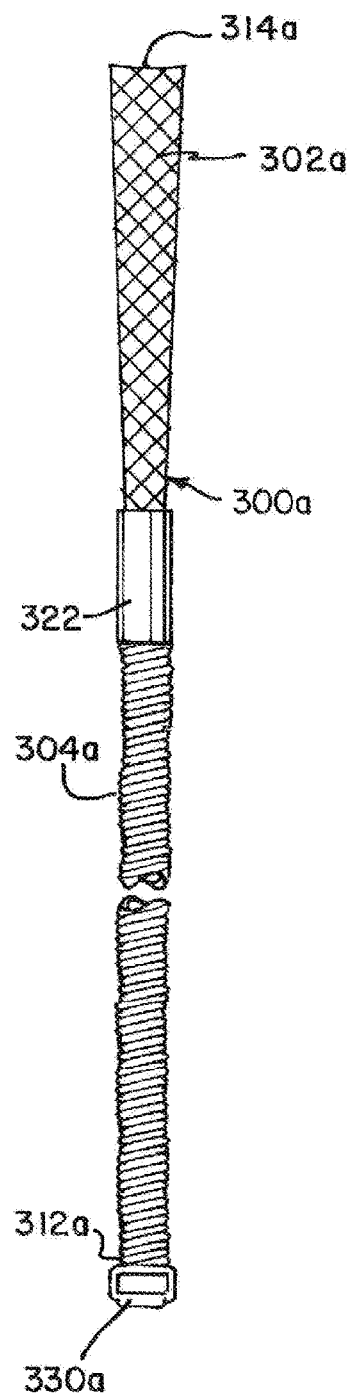
FIGS. 6A and 6B are illustrations of an example implant in a collapsed or delivery configuration (FIG. 6A) and in an implanted or expanded configuration (FIG. 6B) according to aspects of the present invention.

As an alternative to shaping the implant in the delivery configuration such that the expandable braided sack portion 202, 202a envelopes the elongated portion 204, 204a as illustrated in FIGS. 1A and 3A, the implant can be elongated in the delivery configuration as illustrated in FIGS. 4A and 6A. The implant 200 illustrated in FIGS. 1A and 1B can have an essentially identical predetermined shape and/or implanted configuration compared to the implant 300 illustrated in FIGS. 4A and 4B. Likewise, the implant 200a illustrated in FIGS. 3A and 3B can have an essentially identical predetermined shape and/or implanted configuration compared to the implant 300a illustrated in FIGS. 6A and 6B.

Comparing FIGS. 1B and 4B, once implanted, the implants 200, 300 formed of a contiguous tubular braid 210, 310 can be indistinguishable. Likewise, comparing FIGS. 3B and 6B, once implanted, the implants 200a, 300a formed of a braided portion 202a, 302a and an embolic coil 204a, 304a can be indistinguishable. Significant difference between the implants 200, 200a illustrated in FIGS. 1A through 3B and the implants 300, 300a illustrated in FIGS. 4A through 6B include presence of the fold 203, 203a or lack thereof in each respective deformed shape, position of the free open end 226, 226a, 314, 314a during delivery, and process of expanding the expandable braided portion 202, 202a, 302, 302a within the aneurysm 10 during treatment.

Referring to FIGS. 4A and 4B, an implant 300 can include a contiguous tubular braid 310 and a detachment feature 330. As illustrated in FIG. 4A, in the delivery configuration, the detachment feature 330 can be positioned at the proximal end 312 of the implant 300, the elongated portion 304 can extend distally from the detachment feature 330, the expandable braided sack portion 302 can extend distally from the elongated portion 304, and the expandable braided sack portion 302 can have a free open end positioned at the distal end 314 of the implant 300. In the delivery configuration, the implant 300 need not have any discernable boundary to indicate which portion of the tubular braid 310 is the elongated looping portion 304 and which portion is the expandable sack portion 302. Strands at the open end 314 can be free, cut ends; or, alternatively, the strands at the open end 314 be closed, meaning strands within the braid at the free open end 314 are attached to each other by glue, weld, etc. or the strands bend back at the open end 314. Free cut ends can have an advantage of being easier to manufacture while the closed strand ends can have an advantage of being more atraumatic compared to the cut ends.

The implant 300 can include memory shape material and can be pre-shaped such that the expandable braided sack portion 302 forms a globular or spherical shape and a fold 303 separates the elongated looping portion 304 from the expandable braided sack portion 302. The memory shape material can be heat set into the predetermined shape. The implanted shape illustrated in FIG. 4B can be based on the predetermined shape and the shape of the interior wall 14 of the aneurysm 10. To collapse the implant 300 from the predetermined shape (similar to the implanted configuration illustrated in FIG. 4B) to the deformed shape (such as illustrated in FIG. 4A) so that it can be delivered through a catheter, the elongated looping portion 304 can be extended and straightened, the sack portion 302 can be inverted and stretch, and the fold 303 can be opened and flattened.

Referring to FIG. 4B, in the implanted configuration, the expandable braided sack portion 302 can expand to contact a majority of the interior wall 14 of the aneurysm 10. The fold 303 can be positioned near a distal surface 15 of the aneurysm wall 14. The elongated portion 304 can wind within the aneurysm sac 12 and within the braided sack portion 302. By anchoring within the sac 12, the expandable braided sack portion 302 can maintain proper positioning of the implant 300 in the aneurysm 10 and prevent portions of the implant 300, such as the elongated portion 304, from extending into a blood vessel 20a, 20b, 21 or exiting the aneurysm sac 12.

The free end 314 of the expandable braided sack portion 302 can define an opening in the sack when the implant is in the implanted or pre-shaped configuration, and when implanted, the opening can be positioned near the aneurysm neck 16. The opening can be sized such that a portion of the expandable braided sack portion 302 extends across the aneurysm neck 16 to occlude the neck. The elongated portion 304 can enter the aneurysm sac 12 and the sack of the expandable braided sack portion 302 through the opening. The elongated portion 304 can wind or loop around in a complex coiled shape within the expandable braided sack portion 302 and within the aneurysm sac 12. The looped elongated portion 304 can press against the braided sack 302 and provide a force against an interior surface of the braided sack 302 to press an exterior surface of the braided sack 302 to the aneurysm wall 14 to further secure the anchoring of the braided sack 302 within the aneurysm sac 12.

The looped elongated portion 304 can fill a majority of the aneurysm sac 12. The implanted braided sack 302 can be a braided mesh with a porosity sized to inhibit blood flow into the aneurysm 10. The elongated portion can have a substantially uniform circumference 306 along much or all of its length, and it can maintain the substantially uniform circumference 306 as it moves from the delivery configuration to the implanted configuration.

FIGS. 5A through 5E are illustrations of an example implant 300 during implantation steps. FIG. 5A illustrates an implant 300 positioned within a catheter 600 near an aneurysm 10. The aneurysm 10 is illustrated positioned at a bifurcated blood vessel having a stem vessel 21, a first side branch vessel 20a, and a second side blood vessel 20b. The catheter 600 can approach the aneurysm 10 from the stem vessel 21. It is contemplated that example implants 300 disclosed herein can be used for treating sidewall vessels according to methods described herein and as would be understood by a person of ordinary skill in the art. At the instant illustrated in FIG. 5A, the implant 300 is collapsed in the catheter 600. The implant 300 can include memory shape material that is in a deformed shape while it is collapsed in the catheter 600.

FIG. 5B illustrates the implant 300 during implantation. The implant 300 can include an expandable braided sack portion 302 and an elongated embolic portion 304. As the implant 300 is translated distally through the catheter 600, the free open end 314 of the expandable braided sack portion 302 can be positioned at a distal end 314 of the implant 300, the expandable portion 302 can extend proximally from its free open end 314, and the elongated embolic or looping portion 304 can extend proximally from the expandable portion 302. Configured thusly, the expandable portion 302 can be completely expelled from the catheter 600 before the elongated portion 304 begins to exit the catheter 600.

As illustrated in FIG. 5B, the expandable braided sack portion 302 can begin to invert after exiting the catheter 600. The free open end 314 can encircle the braid 310, and portions of the braid 310 can be translated through the opening of the free open end 314. The free end 314 of the implant 300 need not be attached to a delivery system for the braided sack portion 302 to invert. The inversion can be a result of the braided sack portion 302 moving toward its predetermined shape.

FIG. 5C illustrates the implant 300 after the braided sack portion 302 has exited the catheter 600 and expanded within the aneurysm 12. The braided sack portion 302 can expand to contact all or a majority of the interior wall 14 of the aneurysm 10. The braided sack 302 can expand toward the predetermined shape upon exiting the catheter 600. Contact with warm bodily fluid can cause the memory shape material in the braided sack 302 to move to the predetermined shape. The free open end 314 can define an opening in the braided sack 302, and the opening can be positioned at the aneurysm neck 16.

A fold 303 defining a boundary between the expanded braided sack 302 and the elongated portion 304 when in the implant 300 is in the implanted configuration can be positioned near a distal surface 15 of the aneurysm wall 14. At the stage of implantation illustrated in FIG. 5C, the elongated portion 304 can extend from the fold 303, through the opening in the braided sack 302, and into the catheter 600.

FIG. 5D illustrates the elongated portion 304 exiting the catheter 600, entering the braided sack portion 302 through the free open end 314, and winding within the sack 302. As the elongated portion 304 exits the catheter 600, the elongated portion 304 can maintain its circumference 306 as it exits the catheter 600. The elongated portion 304 can wind or loop within the aneurysm sac 12 in response to contacting an interior surface of the expanded braided sack 302. Additionally, or alternatively, the elongated portion 304 can include memory shape material having a predetermined shape and a deformed shape. The predetermined shape can be a complex looped shape, and the deformed shape can be substantially straight. The elongated portion 304 can wind or loop within the aneurysm sac 12 in response to the memory shape material moving from the deformed shape toward the predetermined shape as the elongated portion 304 contacts blood as it exits the catheter 600. Additionally, or alternatively, the elongated portion 304 can include a flexible elastically deformable material having a relaxed shape that is a looped shape. The flexible elastically deformable material can be uncoiled to a substantially straight strand during delivery through a catheter and can collapse into the looped shape upon exiting the catheter 12.

At the instant illustrated in FIG. 5D the detachment feature 330 can remain attached to a delivery system. While the implant 300 is attached to the delivery system, the delivery system can be pulled proximally to withdraw all or portions of the implant 300. The delivery system can subsequently be pushed distally to reposition the implant 300.

FIG. 5E illustrates the implant 300 in a final implanted configuration such as described in relation to FIG. 4B. The detachment feature 330 can be moved distally by the delivery system past the plane of the aneurysm 16, through the open end 314 of the expanded sack portion 302, and into the aneurysm sac 12 prior to detachment from the delivery system. The elongated portion 304 can have a predetermined shape configured to facilitate the movement of the detachment feature 314 past the plane of the aneurysm neck 16 once the implant 300 is implanted. Additionally, or alternatively, the delivery system can be manipulated to place the detachment feature 314 within the sack portion 302. Once the implant 300 is implanted as illustrated in FIG. 5E, the delivery system can be detached and withdrawn, and the microcatheter 600 can be moved or extracted from the patient.

The open end 314 can remain open at the completion of the implantation, and the elongated portion 304, once secured within the sack 302, can be coiled near the opening defined by the open end 314 in such a way that blood flow is obstructed from entering the opening. In other words, sack 302 can occlude a portion of the neck 16 around the perimeter of the neck, and the elongated portion 304 can occlude the neck 16 at the opening in the sack 302 defined by the open end 314.

Figure 6B:
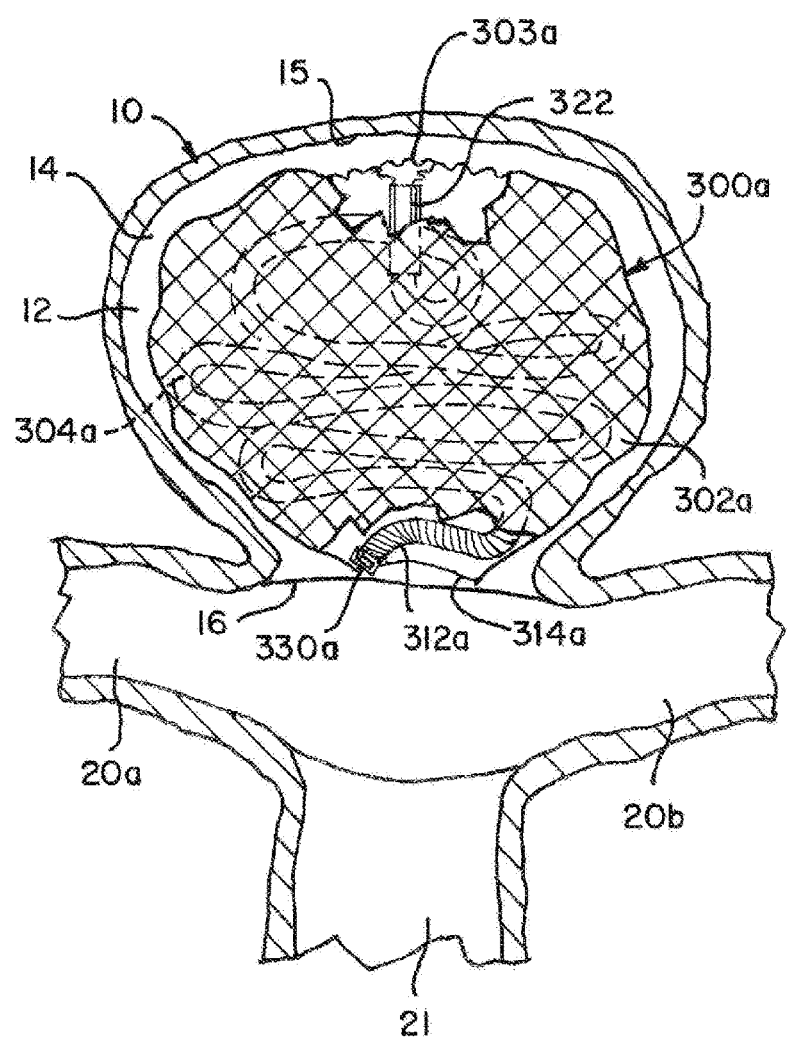

FIG. 6A illustrates an example implant 300a in a collapsed or delivery configuration. In the delivery configuration, the implant 300a can be collapsed to a size that can be delivered to a treatment site through a catheter inserted in vasculature of a patient. FIG. 6B illustrates the example implant 300a illustrated in FIG. 6A in an expanded or implanted configuration. In the implanted configuration, the implant 300a can be positioned in a sac 12 of an aneurysm 10 to divert blood flow from a neck 16 of the aneurysm 10 and fill the sac 12 with embolic material. The embolic material in the aneurysm sac 12 can promote the formation of a thrombotic mass in the aneurysm 10, and the diversion of blood flow from the aneurysm neck 16 can induce venous stasis in the aneurysm and reduce the likelihood that the aneurysm recanalizes after an aneurysm treatment procedure.

Comparing the example implant 300a illustrated in FIGS. 6A and 6B to the implant 300 illustrated in FIGS. 4A through 5E, the elongated portion 304a of the implant 300a in FIGS. 6A and 6B can be an embolic coil 304a rather than a braid 304 as illustrated in FIGS. 4A through 5E. The implant 300a illustrated in FIGS. 6A and 6B can be implanted following a procedure like that illustrated in FIGS. 5A through 5E.

Referring collectively to FIGS. 6A and 6B, the implant 300a can include the embolic coil 304a, an expandable braided sack portion 302a, a detachment feature 330a, and a connecting band 322 joining the embolic coil 304a to the expandable braid 302a. The expandable braided sack portion 302a can be braided. Portions of the implant 300a, including the embolic coil 304a, can be made from a memory shape material having a predetermined shape and a deformed shape. The memory shape material can be in the deformed shape when the implant 300a is in the delivery configuration and can move toward the predetermined shape when the implant 300a is in the expanded or implanted configuration. When expanded or implanted, the memory shape material can be restricted by anatomical geometries and the memory shape material can take a shape that approaches the predetermined shape but does not match the predetermined shape due to the anatomical restrictions.

The detachment feature 330a can be joined to the elongated portion 304a, and the detachment feature 330a can be detachably attached to a delivery system when the implant 300a is delivered through a catheter to a treatment site.

Referring to FIG. 6A, in the delivery configuration, the detachment feature 330a can be positioned at the proximal end 312a of the implant 300a, the elongated portion 304 can extend distally from the detachment feature 330a to the connecting band 322, the braided portion 302a can extend distally from the connecting band 322, and the braided portion 302a can have a free open end 314a positioned at a distal end of the implant 300a. Strands of the braided portion 302a at the open end 314a can be free, cut ends; or, alternatively, the strands at the open end 314a be closed, meaning strands within the braid at the free open end 314a are attached to each other by glue, weld, etc. or the strands bend back at the open end 314a. Free cut ends can have an advantage of being easier to manufacture while the closed strand ends can have an advantage of being more atraumatic compared to the cut ends.

Referring to FIGS. 6A and 6B, the implant 300a can include memory shape material and can be pre-shaped such that the expandable braided sack portion 302a forms a globular or spherical shape and the braid can have a fold 303a near the connecting band 322. The memory shape material can be heat set into the predetermined shape. The implanted shape illustrated in FIG. 6B can be based on the predetermined shape and the shape of the interior wall 14 of the aneurysm 10. To collapse the implant from the predetermined shape so that it can be delivered through a catheter, the embolic coil 304a can be extended and straightened, the sack portion 302a can be inverted and stretched, and the fold 303 can be opened and flattened.

Referring to FIG. 6B, in the implanted configuration, the expandable braided sack portion 302a can expand to contact a majority of the interior wall 14 of the aneurysm 10. The fold 303a can be positioned near a distal surface 15 of the aneurysm wall 14. The embolic coil 304a can wind within the aneurysm sac 12 and within the braided sack portion 302a. By anchoring within the sac 12, the expandable braided sack portion 302a can maintain proper positioning of the implant 300a in the aneurysm 10 and prevent portions of the implant 300a, such as the embolic coil 304a, from extending into a blood vessel 20a, 20b, 21 or exiting the aneurysm sac 12.

The free end 314a of the expandable braided sack portion 302a can define an opening in the sack when the implant 300a is in the implanted or pre-shaped configuration, and when implanted, the opening can be positioned near the aneurysm neck 16. The opening can be sized such that a portion of the expandable braided sack portion 302a extends across the aneurysm neck 16 to occlude the neck. The embolic coil 304a can enter the aneurysm sac 12 and the sack of the expandable braided sack portion 302a through the opening. The elongated portion 304a can wind or loop around in a complex coiled shape within the expandable braided sack portion 302a and within the aneurysm sac 12. The looped elongated portion 304a can press against the braided sack 302a and provide a force against an interior surface of the braided sack 302a to press an exterior surface of the braided sack 302a to the aneurysm wall 14 to further secure the anchoring of the braided sack 302a within the aneurysm sac 12.

The looped embolic coil 304a can fill a majority of the aneurysm sac 12. The implanted braided sack 302a can be a braided mesh with a porosity sized to inhibit blood flow into the aneurysm 10.

FIG. 7 is a flow diagram outlining example method steps for treating an aneurysm. The method steps can be implemented by example devices presented herein or by other means as would be known to one of ordinary skill in the art.

Referring to method 700 outlined in FIG. 7, in step 702, an implant having an expandable portion and an embolic coiling portion can be provided. In step 704, the embolic coiling portion can be detachably attached to a delivery system. In step 706, the implant can be positioned in a microcatheter with the embolic coiling portion extending distally from a proximal end of the implant, the expandable portion extending proximally form the distal end of the implant, and the expandable portion being unattached to the delivery system. In step 708, the distal end of the microcatheter can be positioned near an aneurysm neck. In step 710, the implant can be delivered through the microcatheter to the distal end of the microcatheter. In step 712, the expandable portion can be expelled from the distal end of the microcatheter. In step 714, the expandable portion can expand to contact most of the interior wall of the aneurysm. In step 716, the embolic coiling portion can be expelled from the distal end of the microcatheter. In step 718, the embolic coiling portion can be placed to wind within the expanded expandable portion. In step 720, the embolic coiling portion can be detached from the delivery system.

Referring to method 800 outlined in FIG. 8, in step 810, an implant having an embolic portion and a braided portion having a memory shape material can be provided. In step 820, the braided portion can be shaped to have a spherical predetermined shape. In step 830, the embolic portion can be attached to an implant delivery system so that it can later be detached. In step 840, the implant and the delivery system can be positioned within a microcatheter. In step 850, the implant and delivery system can traverse through the microcatheter while the braided portion is unattached to the delivery system. In step 860, the implant can be expelled from the microcatheter.

Step 840 in method 800, positioning the implant and the delivery system in the microcatheter, can include sub steps as illustrated in FIG. 9. In sub step 842, the braided portion can be collapsed to fit within the microcatheter. In sub step 844, the braided portion can be positioned to extend proximally from a distal end of the implant. In sub step 846, the embolic portion can be positioned to extend distally from a proximal end of the implant. In sub step 848, the delivery system can be positioned to extend proximally form the embolic portion.

Step 860 in method 800, expelling the implant from the microcatheter, can include sub steps as illustrated in FIG. 10. In sub step 862, the braided portion can be expelled from the microcatheter. In sub step 864, the braided portion can be expanded to form a sack shape based on the spherical predetermined shape. In sub step 866, the embolic portion can be expelled from the microcatheter. In sub step 868, the embolic portion can be coiled within the sack shape of the braided portion.

The descriptions contained herein are examples of embodiments of the invention and are not intended to limit the scope of the invention. As described herein, the invention contemplates many variations and modifications of an implant, system, or method that can be used to occlude and fill an aneurysm. Variations can include but are not limited to combining elements of various embodiments, utilizing alternative geometries of elements and components described herein, utilizing alternative materials for each component or element (e.g. radiopaque materials, memory shape materials, etc.), utilizing additional components including components to deliver the implant to a treatment site, position the implant at a treatment site, retract the implant, and/or eject a portion of the implant from a catheter, utilizing additional component to perform functions describe herein, and utilizing additional components to perform functions not described herein, for example. These modifications would be apparent to those having ordinary skill in the art to which this invention relates and are intended to be within the scope of the claims which follow.

The invention claimed is:

1. An implant comprising:
    an expandable braided sack portion comprising a free open end;
    an elongated looping portion joined to the expandable braided sack portion; and
    a detachment feature joined to the elongated looping portion,
    wherein the implant is movable from a delivery configuration sized to traverse through a lumen of a catheter to an implanted configuration sized to secure within an aneurysm,
    wherein in the delivery configuration, the expandable braided sack portion extends from a distal end of the implant, the elongated looping portion extends proximally from the expandable braided sack portion, and the detachment feature is positioned approximate a proximal end of the implant and is detachably attached to a delivery system,
    wherein in the delivery configuration, the expandable braided sack portion is unattached to the delivery system and the free open end is distal to the detachment feature,
    wherein in the delivery configuration, the implant comprises a fold approximate the distal end of the implant, the expandable braided sack portion encompasses at least a portion of the elongated looping portion, and the free open end encircles the elongated looping portion,
    wherein in the implanted configuration, the expandable braided sack portion is sized to contact a majority of an interior wall of the aneurysm, is sized to contain the elongated looping portion, and is sized to occlude at least a portion of a neck of the aneurysm,
    wherein in the implanted configuration, the free open end is positioned to be placed approximate the neck, and
    wherein in the implanted configuration, the elongated looping portion is sized to wind within the expandable braided sack portion.

2. The implant of claim 1 wherein, in the delivery configuration, the free open end is positioned at the distal end of the implant.

3. An implant comprising:
    an expandable braided sack portion comprising a free open end;
    an elongated looping portion joined to the expandable braided sack portion; and
    a detachment feature joined to the elongated looping portion,
    wherein the implant is movable from a delivery configuration sized to traverse through a lumen of a catheter to an implanted configuration sized to secure within an aneurysm,
    wherein in the delivery configuration, the expandable braided sack portion extends from a distal end of the implant, the elongated looping portion extends proximally from the expandable braided sack portion, and the detachment feature is positioned approximate a proximal end of the implant and is detachably attached to a delivery system,
    wherein in the delivery configuration, the expandable braided sack portion is unattached to the delivery system and the free open end is distal to the detachment feature,
    wherein in the implanted configuration, the expandable braided sack portion is sized to contact a majority of an interior wall of the aneurysm, is sized to contain the elongated looping portion, and is sized to occlude at least a portion of a neck of the aneurysm, wherein in the implanted configuration, the free open end is positioned to be placed approximate the neck, wherein in the implanted configuration, the elongated looping portion is sized to wind within the expandable braided sack portion, and wherein in the implanted configuration, a fold defining a boundary between the elongated looping portion and the expandable braided sack portion is positioned to be implanted approximate a distal surface of the interior aneurysm wall.

4. An implant comprising:

an expandable braided sack portion comprising a free open end;

an elongated looping portion joined to the expandable braided sack portion; and a detachment feature joined to the elongated looping portion, wherein the elongated looping portion and the expandable braided sack portion are portions of a contiguous tubular braid, wherein the implant is movable from a delivery configuration sized to traverse through a lumen of a catheter to an implanted configuration sized to secure within an aneurysm, wherein in the delivery configuration, the expandable braided sack portion extends from a distal end of the implant, the elongated looping portion extends proximally from the expandable braided sack portion, and the detachment feature is positioned approximate a proximal end of the implant and is detachably attached to a delivery system, wherein in the delivery configuration, the expandable braided sack portion is unattached to the delivery system and the free open end is distal to the detachment feature, wherein in the implanted configuration, the expandable braided sack portion is sized to contact a majority of an interior wall of the aneurysm, is sized to contain the elongated looping portion, and is sized to occlude at least a portion of a neck of the aneurysm, wherein in the implanted configuration, the free open end is positioned to be placed approximate the neck, wherein in the implanted configuration, the elongated looping portion is sized to wind within the expandable braided sack portion, and wherein in the implanted configuration, the elongated looping portion comprises a substantially uniform circumference along a majority of its length, the length measurable from the detachment feature to a fold defining a boundary between the elongated looping portion and the expandable braided sack portion.

5. The implant of claim 1 wherein the elongated looping portion comprises an embolic coil, wherein the expandable braided sack portion comprises a tubular braid.

6. The implant of claim 1 wherein the implant consists of the expandable braided sack portion, the elongated looping portion, and the detachment feature.

* * * * *